(12) United States Patent
Yoon et al.

(10) Patent No.: US 11,857,946 B2
(45) Date of Patent: Jan. 2, 2024

(54) PREPARING METHOD OF SUPER ABSORBENT POLYMER SHEET AND SUPER ABSORBENT POLYMER SHEET PREPARED THEREFROM

(71) Applicant: LG Chem, Ltd., Seoul (KR)

(72) Inventors: Kiyoul Yoon, Daejeon (KR); Hyeon Choi, Daejeon (KR); Hyosook Joo, Daejeon (KR); Gicheul Kim, Daejeon (KR); Ju Eun Kim, Daejeon (KR)

(73) Assignee: LG Chem, Ltd.

( * ) Notice: Subject to any disclaimer, the term of this patent is extended or adjusted under 35 U.S.C. 154(b) by 508 days.

(21) Appl. No.: 16/772,473

(22) PCT Filed: Dec. 14, 2018

(86) PCT No.: PCT/KR2018/015932
§ 371 (c)(1),
(2) Date: Jun. 12, 2020

(87) PCT Pub. No.: WO2019/117670
PCT Pub. Date: Jun. 20, 2019

(65) Prior Publication Data
US 2020/0384441 A1  Dec. 10, 2020

(30) Foreign Application Priority Data

Dec. 14, 2017  (KR) .................. 10-2017-0172269
Dec. 13, 2018  (KR) .................. 10-2018-0161304

(51) Int. Cl.
*B01J 20/26* (2006.01)
*B01J 20/28* (2006.01)
*B01J 20/30* (2006.01)

(52) U.S. Cl.
CPC ....... *B01J 20/267* (2013.01); *B01J 20/28033* (2013.01); *B01J 20/3064* (2013.01); *B01J 20/3085* (2013.01)

(58) Field of Classification Search
None
See application file for complete search history.

(56) References Cited

U.S. PATENT DOCUMENTS

| | | | |
|---|---|---|---|
| 5,338,766 A * | 8/1994 | Phan .................. | A61L 15/24 521/64 |
| 2005/0137546 A1 | 6/2005 | Joy et al. | |
| 2005/0153123 A1 | 7/2005 | Herfert et al. | |
| 2007/0129517 A1 | 6/2007 | Lang et al. | |
| 2007/0207924 A1 | 9/2007 | Ikeuchi et al. | |
| 2008/0221277 A1* | 9/2008 | Walden .............. | C08F 220/06 525/418 |
| 2009/0191408 A1 | 7/2009 | Tian et al. | |
| 2009/0192481 A1 | 7/2009 | Dodge, II et al. | |
| 2009/0192482 A1* | 7/2009 | Dodge, II .......... | A61L 15/60 524/436 |
| 2009/0239966 A1 | 9/2009 | Matsumoto et al. | |
| 2011/0245436 A1 | 10/2011 | Gartner et al. | |
| 2012/0001122 A1 | 1/2012 | Wattebled et al. | |
| 2014/0054497 A1 | 2/2014 | Wattebled et al. | |
| 2016/0280866 A1 | 9/2016 | Lee et al. | |
| 2016/0337738 A1 | 11/2016 | Hayashi | |
| 2016/0354757 A1 | 12/2016 | Lee et al. | |
| 2018/0043332 A1 | 2/2018 | Lee et al. | |
| 2018/0185820 A1 | 7/2018 | Tada et al. | |
| 2018/0228671 A1 | 8/2018 | Hwang et al. | |
| 2018/0265653 A1 | 9/2018 | Lee et al. | |
| 2020/0164344 A1 | 5/2020 | Kim et al. | |

FOREIGN PATENT DOCUMENTS

| | | |
|---|---|---|
| CN | 1889987 A | 1/2007 |
| CN | 101356202 A | 1/2009 |
| CN | 102361653 A | 2/2012 |
| CN | 103476811 A | 12/2013 |
| CN | 105980464 A | 9/2016 |
| CN | 106164099 A | 11/2016 |
| EP | 1966257 A2 | 9/2008 |
| EP | 2244747 A2 | 11/2010 |
| EP | 3070107 A1 | 9/2016 |
| EP | 3636698 A1 | 4/2020 |
| JP | 2004001355 A | 1/2004 |
| JP | 2007514833 A | 6/2007 |
| JP | 2007529295 A | 10/2007 |
| JP | 2009518469 A | 5/2009 |
| JP | 2012522880 A | 9/2012 |
| JP | 2014516378 A | 7/2014 |
| JP | 2016016667 A | 2/2016 |
| JP | 2016079267 A | 5/2016 |
| JP | 2019518821 A | 7/2019 |
| KR | 20070094741 A | 9/2007 |
| KR | 20120043165 A | 5/2012 |
| KR | 101433681 B1 | 8/2014 |
| KR | 20140133470 A | 11/2014 |
| KR | 20140145810 A | 12/2014 |
| KR | 20150088219 A | 7/2015 |
| KR | 101601990 B1 | 3/2016 |
| KR | 20160056326 A | 5/2016 |
| KR | 101635257 B1 | 6/2016 |

(Continued)

OTHER PUBLICATIONS

Extended European Search Report for Application No. 18889354.9 dated Nov. 25, 2020, 8 pages.

(Continued)

*Primary Examiner* — Tanisha Diggs
(74) *Attorney, Agent, or Firm* — Lerner David LLP

(57) ABSTRACT

The present disclosure relates to a preparing method of a super absorbent polymer sheet and a super absorbent polymer sheet prepared therefrom. The preparing method of a super absorbent polymer sheet of the present disclosure may prepare a porous flexible super absorbent polymer sheet exhibiting high flexibility and fast absorption rate.

10 Claims, 1 Drawing Sheet

(56) References Cited

FOREIGN PATENT DOCUMENTS

| KR | 20160063956 A | 6/2016 |
|---|---|---|
| KR | 20170075624 A | 7/2017 |
| KR | 20170090185 A | 8/2017 |
| KR | 101789350 B1 | 10/2017 |
| KR | 20170132799 A | 12/2017 |
| WO | 2003092757 A1 | 11/2003 |
| WO | 2005063313 A1 | 7/2005 |
| WO | 2007111716 A2 | 10/2007 |
| WO | 2009095810 A2 | 8/2009 |
| WO | 2019050183 A1 | 3/2019 |
| WO | 2019216591 A1 | 11/2019 |
| WO | 2019216592 A1 | 11/2019 |
| WO | 2020067662 A1 | 4/2020 |

OTHER PUBLICATIONS

Search Report dated Mar. 21, 2022 from the Office Action for Chinese Application No. 201880079708.7 dated Mar. 30, 2022, pp. 1-3.
International Search Report from Application No. PCT/KR2018/015932 dated Apr. 3, 2019, 3 pages.
Odian, "Principles of Polymerization", Second Edition, A Wiley-Interscience Publication, John Wiley & Sons, Inc., 1981, p. 203.
Schwalm, "UV Coatings: Basics, Recent Developments and New Applications", Elsevier Science, Dec. 21, 2006, p. 115.

\* cited by examiner

PREPARING METHOD OF SUPER ABSORBENT POLYMER SHEET AND SUPER ABSORBENT POLYMER SHEET PREPARED THEREFROM

CROSS-REFERENCE TO RELATED APPLICATIONS

The present application is a national phase entry under 35 U.S.C. § 371 of International Application No. PCT/KR2018/015932 filed Dec. 14, 2018, which claims priority to Korean Patent Application No. 10-2017-0172269 filed on Dec. 14, 2017 and Korean Patent Application No. 10-2018-0161304 filed on Dec. 13, 2018, the disclosures of which are incorporated herein by reference in their entirety.

BACKGROUND OF THE INVENTION

(a) Field of the Invention

The present disclosure relates to a preparing method of a super absorbent polymer sheet and a super absorbent polymer sheet prepared therefrom.

(b) Description of the Related Art

A super absorbent polymer (SAP) is a type of synthetic polymeric material capable of absorbing 500 to 1000 times its own weight of moisture. Various manufacturers have denominated it with different names, such as SAM (Super Absorbency Material), AGM (Absorbent Gel Material), and the like. Such super absorbent polymers started to be practically applied in sanitary products, and they are now being widely used not only for hygiene products such as disposable diapers for children, sanitary napkins, etc., but also for water retaining soil products for gardening, water stop materials for the civil engineering and construction, sheets for raising seedling, fresh-keeping agents for food distribution fields, materials for poultices, or the like.

In general, hygiene products such as various diapers, sanitary napkins, or pads for urinary incontinence include an absorber containing super absorbent polymer particles. It was common that the absorber mainly includes the super absorbent polymer particles and fluff pulp to properly fasten the super absorbent polymer particles while maintaining the shape of the absorber and hygiene products.

However, due to the presence of the fluff pulp, it was difficult to make the absorber and hygiene products slim and thin, and there was a problem such as poor wearability in which wearer's skin against the hygiene product becomes sweaty. Moreover, the necessity of using a large amount of the fluff pulp, which is mainly obtained from wood as a raw material, has been contrary to the recent environmental protection trend, and it has become one of the main reasons to increase manufacturing costs of the absorbent layer and the hygiene products.

Therefore, in the absorbent layer and the hygiene products industry, many attempts have been made to reduce the amount of fluff pulp used or to provide hygiene products such as so-called pulpless diapers without using the fluff pulp.

Meanwhile, current super absorbent polymers are mostly manufactured and used in the form of powder. This powdery super absorbent polymer has a limited range of use, because it has to be scattered or leaked when manufacturing sanitary materials or in actual use and must be used with a specific type of substrate.

Recently, a preparing method of a super absorbent polymer in the form of fiber has been proposed. However, research on a preparing method of a super absorbent polymer which can be used as a pulpless absorber without deterioration of the absorption performance while exhibiting sufficient flexibility is still required.

SUMMARY OF THE INVENTION

In order to solve the problems, the present disclosure is to provide a super absorbent polymer sheet exhibiting high flexibility and fast absorption rate, and a super absorbent polymer sheet prepared therefrom.

According to one embodiment of the present disclosure, there is provided a preparing method of a super absorbent polymer sheet, including the steps of:

preparing a monomer composition including an acrylic acid-based monomer having at least partially neutralized acidic groups, a comonomer containing polyethylene glycol (methyl ether) (meth)acrylate, an internal cross-linking agent containing a polyol, an encapsulated blowing agent, and a polymerization initiator;

preparing a hydrogel polymer by thermal polymerization or photopolymerization of the monomer composition; and drying the hydrogel polymer to form a super absorbent polymer sheet.

According to another embodiment of the present disclosure, there is provided a super absorbent polymer sheet prepared from the above preparing method.

The super absorbent polymer sheet prepared according to the present disclosure is in the form of a sheet or a film unlike the conventional super absorbent polymer which is in the form of powder, and can be directly applied to products without scattering or leaking while exhibiting flexibility.

In addition, the super absorbent polymer sheet prepared according to the preparing method of the present disclosure has an open pore channel structure in which pores are connected to each other, so that absorption of water by capillary pressure is possible, thereby improving absorption rate and permeability.

As described above, since the super absorbent polymer sheet has high flexibility and fast absorption rate due to inherent physical properties of the super absorbent polymer, it can be applied to various products requiring flexibility and high absorbency.

Further, the super absorbent polymer sheet can be used as a pulpless absorber.

DETAILED DESCRIPTION OF THE EMBODIMENTS

Figure 1:
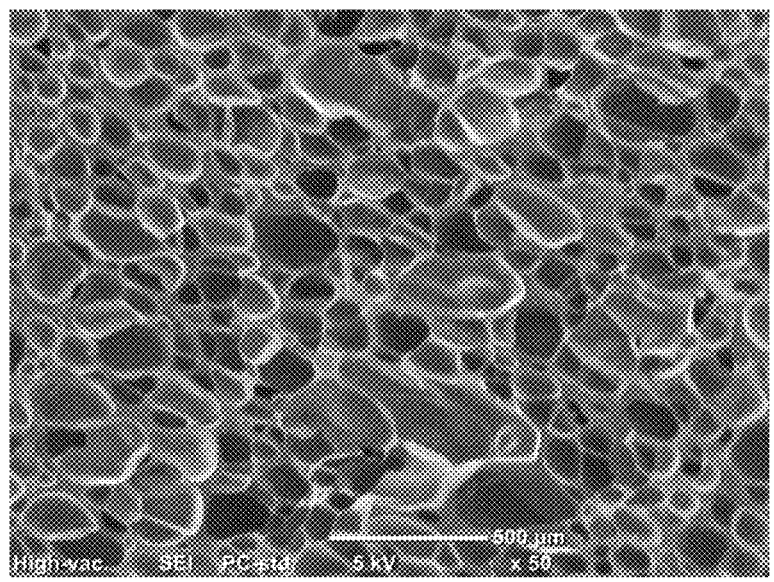
FIG. 1 is a scanning electron microscope (SEM) photograph of a surface of the super absorbent polymer sheet according to Example of the present disclosure.

As the present invention can be variously modified and have various forms, specific embodiments thereof are shown by way of examples and will be described in detail. However, it is not intended to limit the present invention to the particular form disclosed and it should be understood that the present invention includes all modifications, equivalents, and replacements within the idea and technical scope of the present invention.

Hereinafter, the preparing method of a super absorbent polymer sheet according to one embodiment of the present disclosure and the super absorbent polymer sheet prepared therefrom will be described in more detail.

According to one embodiment of the present disclosure, there is provided a preparing method of a super absorbent polymer sheet, including the steps of: preparing a monomer composition including an acrylic acid-based monomer having at least partially neutralized acidic groups, a comonomer containing polyethylene glycol (methyl ether) (meth)acrylate, an internal cross-linking agent containing a polyol, an encapsulated blowing agent, and a polymerization initiator; preparing a hydrogel polymer by thermal polymerization or photopolymerization of the monomer composition; and drying the hydrogel polymer to form a super absorbent polymer sheet.

In the present disclosure, the monomer composition which is a raw material of the super absorbent polymer includes an acrylic acid-based monomer having at least partially neutralized acidic groups, a comonomer containing polyethylene glycol (methyl ether) (meth)acrylate, an internal cross-linking agent containing a polyol, an encapsulated blowing agent, and a polymerization initiator.

First, the acrylic acid-based monomer is a compound represented by the following Chemical Formula 1:

  [Chemical Formula 1]

in Chemical Formula 1, $R^1$ is a C2 to C5 alkyl group having an unsaturated bond, and $M^1$ is a hydrogen atom, a monovalent or divalent metal, an ammonium group, or an organic amine salt.

Preferably, the acrylic acid-based monomer includes at least one selected from the group consisting of acrylic acid, methacrylic acid, and a monovalent metal salt, a divalent metal salt, an ammonium salt, and an organic amine salt thereof.

Herein, the acrylic acid-based monomers may be those having acidic groups which are at least partially neutralized. Preferably, the acrylic acid-based monomer partially neutralized with an alkali substance such as sodium hydroxide, potassium hydroxide, ammonium hydroxide, or the like may be used. A degree of neutralization of the acrylic acid-based monomer may be 40 to 95 mol %, 40 to 80 mol %, or 45 to 75 mol %. The range of the degree of neutralization can be adjusted according to final properties. An excessively high degree of neutralization causes the neutralized monomers to be precipitated, and thus polymerization may not readily occur, whereas an excessively low degree of neutralization not only deteriorates the absorbency of the polymer, but also endows the polymer with hard-to-handle properties, such as those of an elastic rubber.

The concentration of the acrylic acid-based monomer may be about 20 to about 60 wt %, preferably about 40 to about 50 wt %, based on the monomer composition including the raw materials of the super absorbent polymer and the solvent, and it may be appropriately selected in consideration of the reaction time and the reaction conditions. However, when the concentration of the monomer is excessively low, the yield of the super absorbent polymer may become low and there may be a problem in economic efficiency. In contrast, when the concentration is excessively high, it may cause problems in processes that some of the monomer may be extracted or the pulverization efficiency of the prepared hydrogel polymer may be lowered in the pulverizing process, and thus physical properties of the super absorbent polymer may be deteriorated.

The monomer composition of the present disclosure includes polyethylene glycol (methyl ether) (meth)acrylate as a comonomer.

The polyethylene glycol (methyl ether) (meth)acrylate is copolymerized with the acrylic acid-based monomer in the polymerization process to enable polymerization of a super absorbent polymer having a flexible polymer structure.

In order to form an optimized polymer structure, the number of ethylene glycol repeating units in the polyethylene glycol (methyl ether) (meth)acrylate may be 3 to 100, 3 to 80, or 3 to 50.

The polyethylene glycol (methyl ether) (meth)acrylate may be included in an amount of 5 to 40 parts by weight, preferably 5 to 30 parts by weight, more preferably 10 to 30 parts by weight, based on 100 parts by weight of the acrylic acid-based monomer. When the comonomer is included too little, there may be no effect of improving flexibility, and when included too much, there may be a decrease in the absorption rate and absorption ability. Therefore, the comonomer may be included within the above range.

The monomer composition of the present disclosure includes a polyol as an internal cross-linking agent.

The polyol cross-links with the acrylic acid-based monomer and the comonomer to form a flexible polymer structure, and may also contribute to increase the moisture content of the super absorbent polymer sheet due to its hygroscopicity.

Examples of the polyol may include ethylene glycol, propylene glycol, 1,3-propanediol, 1,4-butanediol, 1,6-hexanediol, 1,2-hexanediol, 1,3-hexanediol, 2-methyl-1,3-propanediol, 2,5-hexanediol, 2-methyl-1,3-pentanediol, 2-methyl-2,4-pentanediol, tripropylene glycol and glycerol, and the glycerol is preferable.

The polyol may be included in an amount of 10 to 100 parts by weight, preferably 20 to 80 parts by weight, more preferably 30 to 60 parts by weight, based on 100 parts by weight of the acrylic acid-based monomer. When the polyol is included too little, there may be no effect of improving the moisture content, and when included too much, there may be a decrease in the absorption rate and absorption ability. Therefore, the polyol may be included within the above range.

The monomer composition of the present disclosure may further include other internal cross-linking agents in addition to the polyol. As the internal cross-linking agent, a poly(meth)acrylate-based compound of polyol, for example, a poly(meth)acrylate-based compound of C2 to C10 polyol may be used. More specifically, trimethylolpropane tri(meth)acrylate, ethyleneglycol di(meth)acrylate, polyethyleneglycol di(meth)acrylate, propyleneglycol di(meth)acrylate, polypropyleneglycol di(meth)acrylate, butanediol di(meth)acrylate, butyleneglycol di(meth)acrylate, diethyleneglycol di(meth)acrylate, hexanediol di(meth)acrylate, triethyleneglycol di(meth)acrylate, tripropyleneglycol di(meth)acrylate, tetraethyleneglycol di(meth)acrylate, dipentaerythritol pentaacrylate, glycerin tri(meth)acrylate or pentaerythol tetraacrylate may be used. And, the polyethyleneglycol diacrylate is preferable.

The monomer composition of the present disclosure includes an encapsulated blowing agent.

The encapsulated blowing agent is present in an encapsulated state during polymerization of the monomer composition, and is then foamed by the heat applied during a drying process described later. As a result, pores having an appropriate size are formed in the polymer structure of the super absorbent polymer so that the super absorbent polymer sheet can have an open pore channel structure.

The encapsulated blowing agent may have a structure including a core containing a hydrocarbon, and a shell surrounding the core and formed of a thermoplastic resin. The encapsulated blowing agent varies in expansion characteristics depending on the components constituting the core and the shell, and the weight and diameter of each component. By controlling them, the blowing agent may expand to a desired size and control porosity of the super absorbent polymer sheet.

Meanwhile, it is necessary to first confirm expansion characteristics of the encapsulated blowing agent in order to determine whether pores having a desired size are formed. However, the form in which the blowing agent encapsulated in the super absorbent polymer is foamed may vary depending on manufacturing conditions of the super absorbent polymer, and thus it is difficult to define it. Therefore, it is possible to determine whether the blowing agent is suitable for forming the desired pores, by first foaming the encapsulated blowing agent in air to check an expansion ratio and a size.

Specifically, the encapsulated blowing agent is applied on a glass petri dish and then heated at 150° C. for 10 minutes in air to expand the encapsulating blowing agent. When the encapsulated blowing agent exhibits a maximum expansion ratio in air of 3 to 15 times, 5 to 15 times or 8.5 to 10 times, it is suitable for forming an open pore structure in the preparing method of a super absorbent polymer sheet of the present disclosure.

The encapsulated blowing agent may have an average diameter of 5 to 50 μm, 5 to 30 μm, 5 to 20 μm, or 7 to 17 μm. It can be determined that the encapsulated blowing agent is suitable to achieve appropriate porosity when exhibiting such an average diameter.

In addition, it can be determined that the encapsulated blowing agent is suitable for forming a suitable open pore structure in the preparing method of a super absorbent polymer sheet of the present disclosure, when exhibiting a maximum expanded diameter of 20 to 190 μm, 50 to 190 μm, 70 to 190 μm, or 75 to 190 μm in air.

The maximum expansion ratio and the maximum expanded diameter in air of the encapsulated blowing agent will be described in more detail in the Examples below.

The hydrocarbon constituting the core of the encapsulated blowing agent may be at least one selected from the group consisting of n-propane, n-butane, iso-butane, cyclobutane, n-pentane, iso-pentane, cyclopentane, n-hexane, iso-hexane, cyclohexane, n-heptane, iso-heptane, cycloheptane, n-octane, iso-octane and cyclooctane. Among these, C3 to C5 hydrocarbons (n-propane, n-butane, iso-butane, cyclobutane, n-pentane, iso-pentane, cyclopentane) are suitable for forming pores having the above-described sizes, and the iso-butane may be most suitable.

In addition, the thermoplastic resin constituting the shell of the encapsulated blowing agent may be a polymer formed from at least one monomer selected from the group consisting of (meth)acrylate, (meth)acrylonitrile, aromatic vinyl, vinyl acetate, vinyl halide and vinylidene halide. Among these, a polymer of the (meth)acrylate and (meth)acrylonitrile may be most suitable for forming pores having the above-described sizes.

The encapsulated blowing agent may include 10 to 30 wt % of a hydrocarbon based on a total weight of the encapsulated blowing agent. It may be most suitable for forming an open pore structure within this range.

The encapsulated blowing agent may be prepared and used, or a commercially available blowing agent satisfying the above conditions may be used.

The encapsulated blowing agent may be included in an amount of 0.1 to 20 parts by weight, preferably 0.5 to 10 parts by weight, more preferably 1 to 10 parts by weight, based on 100 parts by weight of the acrylic acid-based monomer. When the encapsulated blowing agent is included too little, the open pore structure may not be properly formed, and when included too much, there may be a decrease in strength of the super absorbent polymer due to its high porosity. Therefore, the encapsulated blowing agent may be included within the above range.

In the preparing method of a super absorbent polymer sheet of the present disclosure, a polymerization initiator that has been generally used for preparing a super absorbent polymer can be applied without particular limitations.

Specifically, the polymerization initiator may be an initiator for thermal polymerization or an initiator for photopolymerization by UV radiation according to the polymerization method. However, even when the photopolymerization method is applied thereto, a certain amount of heat is generated by UV radiation and the like, and some heat occurs as the polymerization reaction, an exothermal reaction, progresses. Therefore, the composition may additionally include the thermal polymerization initiator.

Herein, any compound which can form a radical by light such as UV rays may be used as the photopolymerization initiator without limitation.

For example, the photopolymerization initiator may be one or more compounds selected from the group consisting of benzoin ether, dialkyl acetophenone, hydroxyl alkylketone, phenyl glyoxylate, benzyl dimethyl ketal, acyl phosphine, and α-aminoketone. Further, as the specific example of acyl phosphine, commercial Lucirin TPO, namely, 2,4,6-trimethyl-benzoyl-trimethyl phosphine oxide, may be used. More various photopolymerization initiators are well disclosed in "UV Coatings: Basics, Recent Developments and New Application (Elsevier, 2007)" written by Reinhold Schwalm, p 115, and the present invention is not limited thereto.

The concentration of the photopolymerization initiator in the monomer composition may be about 0.01 to about 1.0 wt %. When the concentration of the photopolymerization initiator is excessively low, the polymerization rate may become slow, and when the concentration is excessively high, the molecular weight of the super absorbent polymer may become low and the properties may be uneven.

Furthermore, as the thermal polymerization initiator, one or more initiators selected from the group consisting of a persulfate-based initiator, an azo-based initiator, hydrogen peroxide, and ascorbic acid may be used. Specifically, sodium persulfate ($Na_2S_2O_8$), potassium persulfate ($K_2S_2O_8$), ammonium persulfate (($NH_4)_2S_2O_8$), and the like may be used as examples of the persulfate-based initiators; and 2,2-azobis-(2-amidinopropane)dihydrochloride, 2,2-azobis-(N,N-dimethylene)isobutyramidinedihydrochloride, 2-(carbamoylazo)isobutylonitrile, 2,2-azobis-[2-(2-imidazolin-2-yl)propane]dihydrochloride, 4,4-azobis-(4-cyanovaleric acid), and the like may be used as examples of azo-based initiators. More various thermal polymerization initiators are well disclosed in "Principle of Polymerization (Wiley, 1981)" written by Odian, p 203, and the present invention is not limited thereto.

The concentration of the thermal polymerization initiator included in the monomer composition may be about 0.001 to about 0.5 wt %. When the concentration of the thermal polymerization initiator is excessively low, additional thermal polymerization hardly occurs and there may be less effect according to the addition of the thermal polymerization initiator. When the concentration of the thermal polymerization initiator is excessively high, the molecular weight of the super absorbent polymer may become low and the properties may be uneven.

In the preparing method of the present disclosure, the monomer composition may include an additive such as a thickener, a plasticizer, a preservation stabilizer, an antioxidant, and the like, if necessary.

The raw materials such as the acrylic acid-based monomer, the comonomer, the internal cross-linking agent, the polymerization initiator, and the additive may be prepared in the form of a monomer composition solution dissolved in a solvent. The solvent may be included in the monomer composition at a residual quantity except for the above components.

At this time, any solvent which can dissolve the components may be used without limitation, and for example, one or more solvents selected from water, ethanol, ethyleneglycol, diethyleneglycol, triethyleneglycol, 1,4-butanediol, propyleneglycol, ethyleneglycol monobutylether, propyleneglycol monomethylether, propyleneglycol monomethylether acetate, methylethylketone, acetone, methylamylketone, cyclohexanone, cyclopentanone, diethyleneglycol monomethylether, diethyleneglycol ethylether, toluene, xylene, butyrolactone, carbitol, methylcellosolve acetate, N,N-dimethylacetamide, and the like may be used alone or in combination.

Subsequently, a hydrogel polymer is prepared by thermal polymerization or photopolymerization of the monomer composition.

Meanwhile, the method of preparing the hydrogel polymer by thermal polymerization or photopolymerization of the monomer composition is not particularly limited if it is a common polymerization method for preparing a super absorbent polymer.

Specifically, the polymerization method is largely divided into the thermal polymerization and the photopolymerization according to the energy source of the polymerization. In the case of thermal polymerization, it is generally carried out in a reactor having a kneading spindle, such as a kneader. In the case of photopolymerization, it may be carried out in a reactor equipped with a movable conveyor belt. However, the polymerization method is just an example, and the present invention is not limited thereto.

Generally, the moisture content of the hydrogel polymer obtained by the above method may be about 40 to about 80 wt %. At this time, "moisture content" in the present description is the content of moisture in the entire weight of the hydrogel polymer, and it means a value of which the weight of the dried polymer is subtracted from the weight of the hydrogel polymer. Specifically, the moisture content is defined as a value calculated from the weight loss due to moisture evaporation from the polymer in the process of increasing the temperature of the polymer and drying the same through infrared heating. At this time, the drying condition for measuring the moisture content is that the temperature is increased to about 180° C. and maintained at 180° C., and the total drying time is 20 min including 5 min of a heating step.

Subsequently, the hydrogel polymer is formed into a sheet form and dried to form a super absorbent polymer sheet.

The drying step may be carried out at a temperature of about 120 to 250° C. When the drying temperature is lower than 120° C., the drying time may become excessively long and the properties of the super absorbent polymer finally prepared may decrease. And when the drying temperature is higher than 250° C., the surface of the polymer is excessively dried, and the properties of the super absorbent polymer finally prepared may decrease. Therefore, the drying step may be preferably carried out at a temperature of 120 to 250° C., more preferably at a temperature of 140 to 200° C.

Meanwhile, the drying step may be carried out for about 20 to 90 minutes in consideration of process efficiency, but it is not limited thereto.

A drying method in the drying step is not particularly limited if it has been generally used in the drying process of the hydrogel polymer. Specifically, the drying step may be carried out by the method of hot air provision, infrared radiation, microwave radiation, UV ray radiation, and the like.

The moisture content of the super absorbent polymer sheet after the drying step may be about 10 wt % or more, for example, about 10 to about 40 wt %, or about 15 to about 30 wt %. When the moisture content of the super absorbent polymer sheet is in the above range, flexibility of the sheet can be ensured.

According to one embodiment of the present disclosure, the super absorbent polymer sheet may have a thickness of about 100 μm or more, 1,000 μm or more or 5,000 μm or more, and about 10 cm or less, about 5 cm or less, or about 1 cm or less. When the thickness of the super absorbent polymer sheet is excessively thin, strength may be low to make the sheet torn. When it is excessively thick, drying and processing may be difficult. From this point of view, it may be preferable to make the thickness within the range described above.

According to the preparing method of a super absorbent polymer sheet of the present disclosure, since the super absorbent polymer sheet is in a sheet form with an open pore channel structure in which at least a part of pores are connected to each other, absorption of water by capillary pressure is possible, so that absorption rate and permeability are improved. Therefore, the super absorbent polymer sheet can be provided as a pulpless absorber.

According to another embodiment of the present disclosure, a super absorbent polymer sheet prepared by the above preparing method is provided.

The super absorbent polymer sheet has an open pore channel structure in which at least a part of pores are connected to each other, so that absorption of water by capillary pressure is possible. Accordingly, absorption rate and permeability can be improved as compared with the conventional powdery super absorbent polymer.

In addition, the super absorbent polymer sheet may have centrifuge retention capacity (CRC) of about 10 to about 40 g/g, preferably about 15 to about 25 g/g, measured in accordance with EDANA WSP 241.2.

Moreover, the super absorbent polymer sheet may have absorbency under pressure (AUP) at 0.7 psi of about 5 to about 20 g/g, preferably about 7 to about 15 g/g, measured in accordance with EDANA WSP 242.2.

As described above, the super absorbent polymer sheet of the present disclosure has excellent absorption properties and permeability, and can be used as a pulpless absorber.

Hereinafter, the function and effect of the present invention will be described in more detail through specific examples of the present invention. However, these examples are for illustrative purposes only, and the invention is not intended to be limited by these examples.

EXAMPLES

Preparation of Super Absorbent Polymer Sheet

Example 1

35.3 g of acrylic acid, 43.5 g of sodium hydroxide (NaOH, 30 wt % solution) and 7.7 g of water were mixed to prepare a neutralized solution in which about 70 mol % of the acrylic acid is neutralized (solid content: 56 wt %).

7.1 g of polyethylene glycol (methyl ether) (meth)acrylate (product name: FA-401, manufacturer: Hannong Chemicals) as a comonomer, 10 g of glycerol, 0.06 g of polyethylene glycol diacrylate (MW=330, manufacturer: Aldrich) and 0.51 g of an encapsulated blowing agent (36D grade, manufacturer: Matsumoto) were added to the neutralized solution to prepare a monomer composition.

The monomer composition was high-shear blended for about 10 minutes at 500 rpm using a mechanical mixer.

Thereafter, the mixture was added through a feeder of a polymerization reactor to carry out polymerization to form a hydrogel polymer. At this time, the temperature of the polymerization reactor was kept at 100° C., the maximum temperature during the polymerization was 110° C., and the polymerization was performed for 10 minutes.

Subsequently, the hydrogel polymer was dried in a hot-air drier at 140° C. for 30 minutes, and cut into a sheet form (thickness: 5,000 μm) using a cutter.

In the super absorbent polymer sheet, centrifuge retention capacity (CRC) measured in accordance with EDANA WSP 241.2 was 22.7 g/g, and absorbency under pressure (AUP) at 0.7 psi measured in accordance with EDANA WSP 242.2 was 11.0 g/g.

Example 2

A super absorbent polymer sheet was prepared in the same manner as in Example 1, except that 20 g of glycerol was used.

Example 3

A super absorbent polymer sheet was prepared in the same manner as in Example 1, except that 2.5 g of the encapsulated blowing agent was used.

Comparative Example 1

A super absorbent polymer sheet was prepared in the same manner as in Example 1, except that the encapsulated blowing and glycerol were not used.

In the super absorbent polymer sheet, centrifuge retention capacity (CRC) measured in accordance with EDANA WSP 241.2 was 26.0 g/g, and absorbency under pressure (AUP) at 0.7 psi measured in accordance with EDANA WSP 242.2 was 12.7 g/g.

Comparative Example 2

A super absorbent polymer sheet was prepared in the same manner as in Example 1, except that polyethylene glycol (methyl ether) (meth)acrylate and glycerol were not used.

Comparative Example 3

A super absorbent polymer sheet was prepared in the same manner as in Example 1, except that glycerol was not used.

Comparative Example 4

A super absorbent polymer sheet was prepared in the same manner as in Example 1, except that the encapsulated blowing was not used.

Comparative Example 5

A super absorbent polymer sheet was prepared in the same manner as in Example 1, except that 7.1 g of poly (ethylene oxide) (PEO, manufacturer: Sigma-Aldrich, Mw=300,000 g/mol) was used instead of 7.1 g of polyethylene glycol (methyl ether) (meth)acrylate (product name: FA-401, manufacturer: Hannong Chemicals).

EXPERIMENTAL EXAMPLES

Evaluation of Characteristics of Super Absorbent Polymer Sheet (1) Cross Section of Super Absorbent Polymer Sheet FIG. 1 is a scanning electron microscope (SEM) photograph of a cross section of the super absorbent polymer sheet according to Example 1 of the present disclosure.

Figure 2:
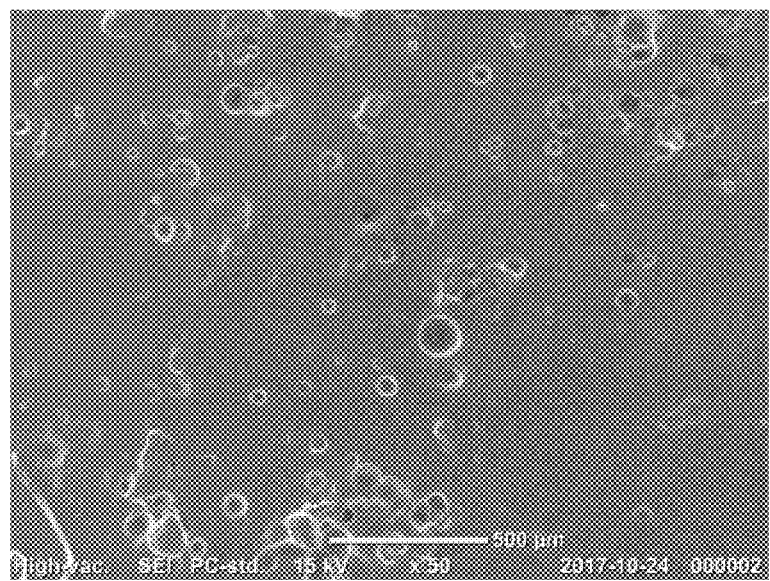
FIG. 2 is a scanning electron microscope (SEM) photograph of a surface of the super absorbent polymer sheet according to Comparative Example of the present disclosure.

FIG. 2 is a scanning electron microscope (SEM) photograph of a cross section of the super absorbent polymer sheet according to Comparative Example 1 of the present disclosure.

Comparing FIG. 1 and FIG. 2, it was confirmed that an open pore channel structure was formed on the surface of the super absorbent polymer sheet according to Example 1 of the present disclosure, but such a structure could not be observed in FIG. 2.

(2) Flexibility

The super absorbent polymer sheet was folded in half and then unfolded. Thereafter, it was evaluated as ○ when returning to the original sheet state, and it was evaluated as X when the folded part did not return to the original sheet state due to cracking or breaking.

The properties of the super absorbent polymer sheets prepared in Examples 1 to 3 and Comparative Examples 1 to 5 were evaluated and shown in Table 1 below.

TABLE 1

|  | Ex. 1 | Ex. 2 | Ex. 3 | Comp. Ex. 1 | Comp. Ex. 2 | Comp. Ex. 3 | Comp. Ex. 4 | Comp. Ex. 5 |
|---|---|---|---|---|---|---|---|---|
| Thickness (μm) | 5,000 μm | 5,000 μm | 5,000 μm | 4,000 μm | 5,000 μm | 5,000 μm | 5,000 μm | 4,000 μm |
| Moisture content (%) | 24.80% | 21.10% | 20.30% | 27.00% | 22.30% | 8.50% | 25.1% | 28.5% |

TABLE 1-continued

|  | Ex. 1 | Ex. 2 | Ex. 3 | Comp. Ex. 1 | Comp. Ex. 2 | Comp. Ex. 3 | Comp. Ex. 4 | Comp. Ex. 5 |
|---|---|---|---|---|---|---|---|---|
| SEM observation of pore structure | ○ | ○ | ○ | x | ○ | ○ | x | x |
| Flexibility | ○ | ○ | ○ | ○ | x | x | x | x |

Referring to Table 1, the super absorbent polymer prepared according to the preparing method of the present disclosure had an open pore channel structure and excellent flexibility.

However, the super absorbent polymers prepared according to Comparative Examples 1 to 5 were found to be difficult to use in a sheet form due to a lack of flexibility, or no open pore channel structure was observed.

What is claimed is:

1. A preparing method of a super absorbent polymer sheet, comprising:
    preparing a monomer composition comprising an acrylic acid-based monomer having at least partially neutralized acidic groups, a comonomer containing polyethylene glycol (methyl ether) (meth)acrylate, an internal cross-linking agent containing a polyol, an encapsulated blowing agent, and a polymerization initiator;
    preparing a hydrogel polymer by thermal polymerization or photopolymerization of the monomer composition; and
    drying the hydrogel polymer to form a super absorbent polymer sheet,
    wherein the encapsulated blowing agent is present in an encapsulated state during the preparing the monomer composition and during the thermal polymerization or the photopolymerization, and is expanded during the drying the hydrogel polymer.

2. The preparing method of a super absorbent polymer sheet of claim 1,
    wherein the polyethylene glycol (methyl ether) (meth) acrylate is included in an amount of 5 to 40 parts by weight based on 100 parts by weight of the acrylic acid-based monomer.

3. The preparing method of a super absorbent polymer sheet of claim 1,
    wherein the polyol comprises at least one of ethylene glycol, propylene glycol, 1,3-propanediol, 1,4-butanediol, 1,6-hexanediol, 1,2-hexanediol, 1,3-hexanediol, 2-methyl-1,3-propanediol, 2,5-hexanediol, 2-methyl-1,3-pentanediol, 2-methyl-2,4-pentanediol, tripropylene glycol or glycerol.

4. The preparing method of a super absorbent polymer sheet of claim 1,
    wherein the polyol is included in an amount of 10 to 100 parts by weight based on 100 parts by weight of the acrylic acid-based monomer.

5. The preparing method of a super absorbent polymer sheet of claim 1,
    wherein the encapsulated blowing agent has an average diameter of 2 to 50 μm.

6. The preparing method of a super absorbent polymer sheet of claim 1,
    wherein the encapsulated blowing agent has an expansion ratio of 3 to 15 times in air.

7. The preparing method of a super absorbent polymer sheet of claim 1,
    wherein the encapsulated blowing agent has a structure comprising a core containing a hydrocarbon and a shell surrounding the core and formed of a thermoplastic resin.

8. The preparing method of a super absorbent polymer sheet of claim 7,
    wherein the hydrocarbon is at least one selected from the group consisting of n-propane, n-butane, iso-butane, cyclobutane, n-pentane, iso-pentane, cyclopentane, n-hexane, iso-hexane, cyclohexane, n-heptane, iso-heptane, cycloheptane, n-octane, iso-octane and cyclooctane.

9. The preparing method of a super absorbent polymer sheet of claim 7,
    wherein the thermoplastic resin is a polymer formed from at least one monomer selected from the group consisting of (meth)acrylate, (meth)acrylonitrile, aromatic vinyl, vinyl acetate, vinyl halide and vinylidene halide.

10. The preparing method of a super absorbent polymer sheet of claim 1,
    wherein the encapsulated blowing agent is included in an amount of 0.1 to 20 parts by weight based on 100 parts by weight of the acrylic acid-based monomer.

* * * * *